(12) United States Patent
Brushey

(10) Patent No.: US 7,805,188 B2
(45) Date of Patent: Sep. 28, 2010

(54) ANESTHESIA CONDUCTION CATHETER FOR DELIVERY OF ELECTRICAL STIMULUS

(75) Inventor: Stephen Brushey, Pittsburgh, PA (US)

(73) Assignee: Micor, Inc., Bethlehem, PA (US)

( * ) Notice: Subject to any disclaimer, the term of this patent is extended or adjusted under 35 U.S.C. 154(b) by 1109 days.

(21) Appl. No.: 10/797,958

(22) Filed: Mar. 10, 2004

(65) Prior Publication Data

US 2004/0210295 A1 Oct. 21, 2004

Related U.S. Application Data

(60) Continuation-in-part of application No. 10/651,728, filed on Aug. 29, 2003, now Pat. No. 7,462,177, which is a division of application No. 09/816,440, filed on Mar. 23, 2001, now Pat. No. 6,676,643.

(60) Provisional application No. 60/191,726, filed on Mar. 24, 2000.

(51) Int. Cl.
*A61B 17/20* (2006.01)
(52) U.S. Cl. .............. 604/21; 604/19; 604/20
(58) Field of Classification Search ........... 604/21, 604/19, 20
See application file for complete search history.

(56) References Cited

U.S. PATENT DOCUMENTS

| 5,899,891 | A | 5/1999 | Racz |
| 5,947,940 | A * | 9/1999 | Beisel .................. 604/526 |
| 6,104,960 | A | 8/2000 | Duysens et al. |
| 6,146,380 | A | 11/2000 | Racz et al. |
| 6,456,874 | B1 * | 9/2002 | Hafer et al. .................. 604/21 |
| 6,626,885 | B2 | 9/2003 | Massengale |
| 6,676,643 | B2 * | 1/2004 | Brushey .................. 604/264 |
| 6,706,016 | B2 | 3/2004 | Cory et al. |
| 7,386,341 | B2 * | 6/2008 | Hafer et al. .................. 607/3 |
| 2002/0052576 | A1 * | 5/2002 | Massengale .......... 604/164.01 |
| 2002/0198568 | A1 | 12/2002 | Hafer et al. |

FOREIGN PATENT DOCUMENTS

DE 31 02 142 A1 1/1981

(Continued)

OTHER PUBLICATIONS

Stanley J. Sarnoff, M.D. and L. Charlotte Sarnoff, Prolonged Peripheral Nerve Block By Means of Indwelling Plastic Cathether. Treatment of Hiccup, Anesthesiology, May 1951, pp. 270-275, vol. 12,The American Society of Anesthesiologists, Inc.
Stanley J. Sarnoff, M.D., Functional Localization of Intraspinal Catheters, Anesthesiology, May 1950, pp. 360-366, vol. 11, The American Society of Anesthesiologists, Inc.

(Continued)

*Primary Examiner*—Nicholas D Lucchesi
*Assistant Examiner*—Laura A Bouchelle
(74) *Attorney, Agent, or Firm*—RatnerPrestia

(57) ABSTRACT

A catheter is comprised of a flexible cylindrical tube defining a proximal portion and a distal portion terminating in a distal tip. The tube has a plurality of openings formed therethrough to form a diffusion area. The catheter includes a conductive end cap enclosing a distal tip. A flexible conductive member is attached to the conductive end cap and extends to the proximal portion where it is attached to the inside diameter of the flexible tube. The member is movable within the tube. Because of the rules governing abstracts, this abstract should not be relied upon in construing the claims.

33 Claims, 9 Drawing Sheets

| | FOREIGN PATENT DOCUMENTS | | |
|----|----|----|----|
| EP | 0 759 307 A2 | 8/1996 | |
| EP | 0 966 922 A1 | 5/1999 | |
| EP | 1 002 500 A1 | 5/2000 | |
| WO | WO 98/33547 | 8/1998 | |
| WO | WO 99/04705 | 2/1999 | |
| WO | WO 01/70322 | 9/2001 | |
| WO | WO 2004/103435 | 12/2004 | |

OTHER PUBLICATIONS

C. Pham-Dang, M.D., et al, Continuous Peripheral Nerve Blocks With Stimulating Catheters, Reg. Anesthesia and Pain Medicine, Mar.-Apr. 2003, 79-82, vol. 28, No. 2.

Letters to the Editor of Anesth. Analg. 1999, 533-4, 3 pgs.

Letters to the Editor of Anesth. Analg. 1998, 228,1 pg.

* cited by examiner

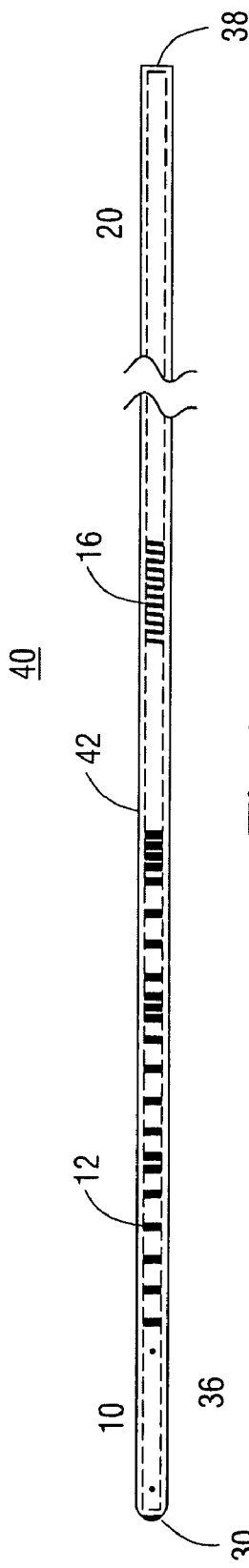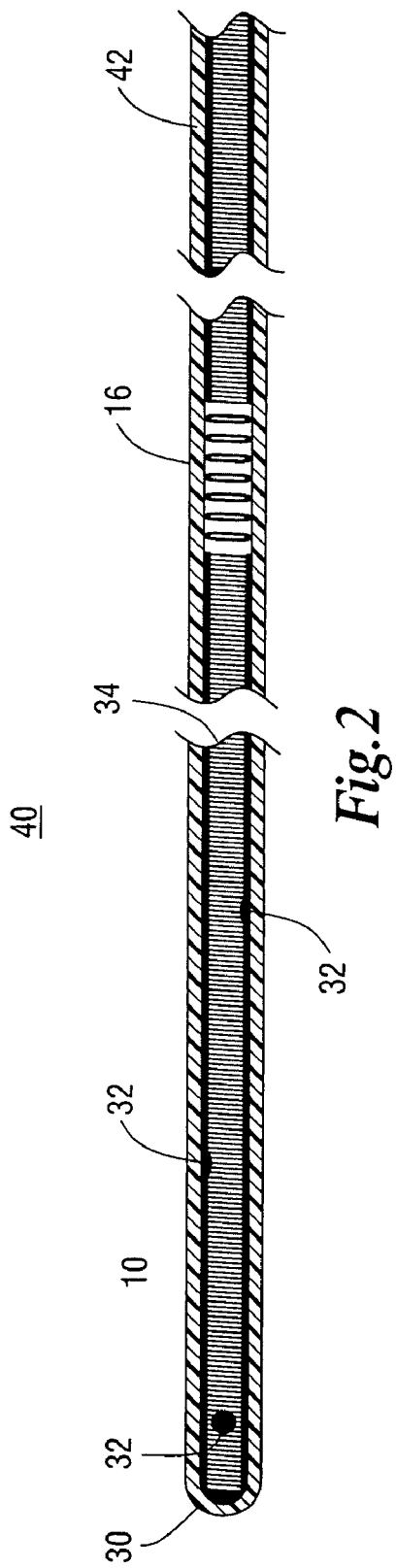

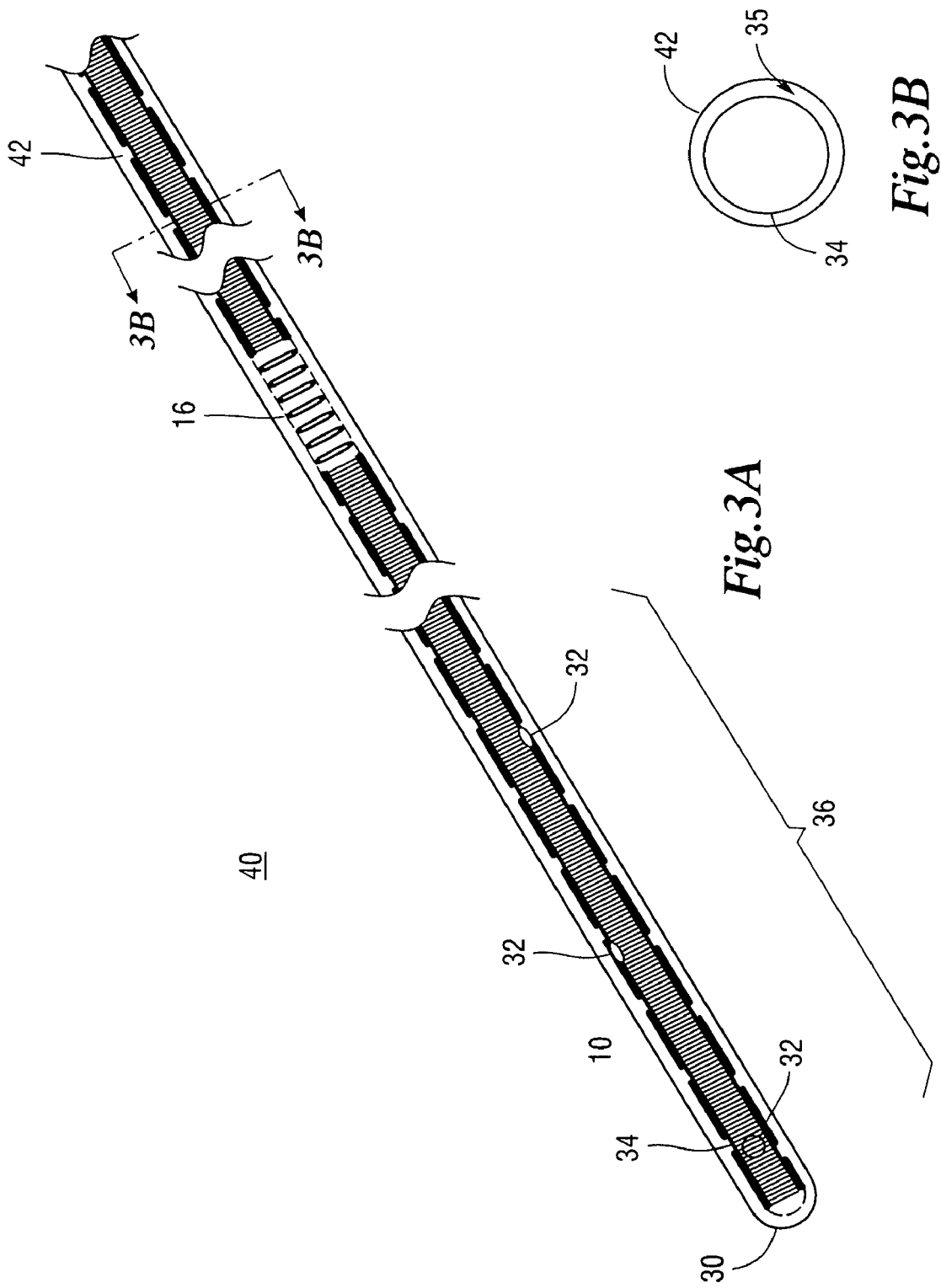

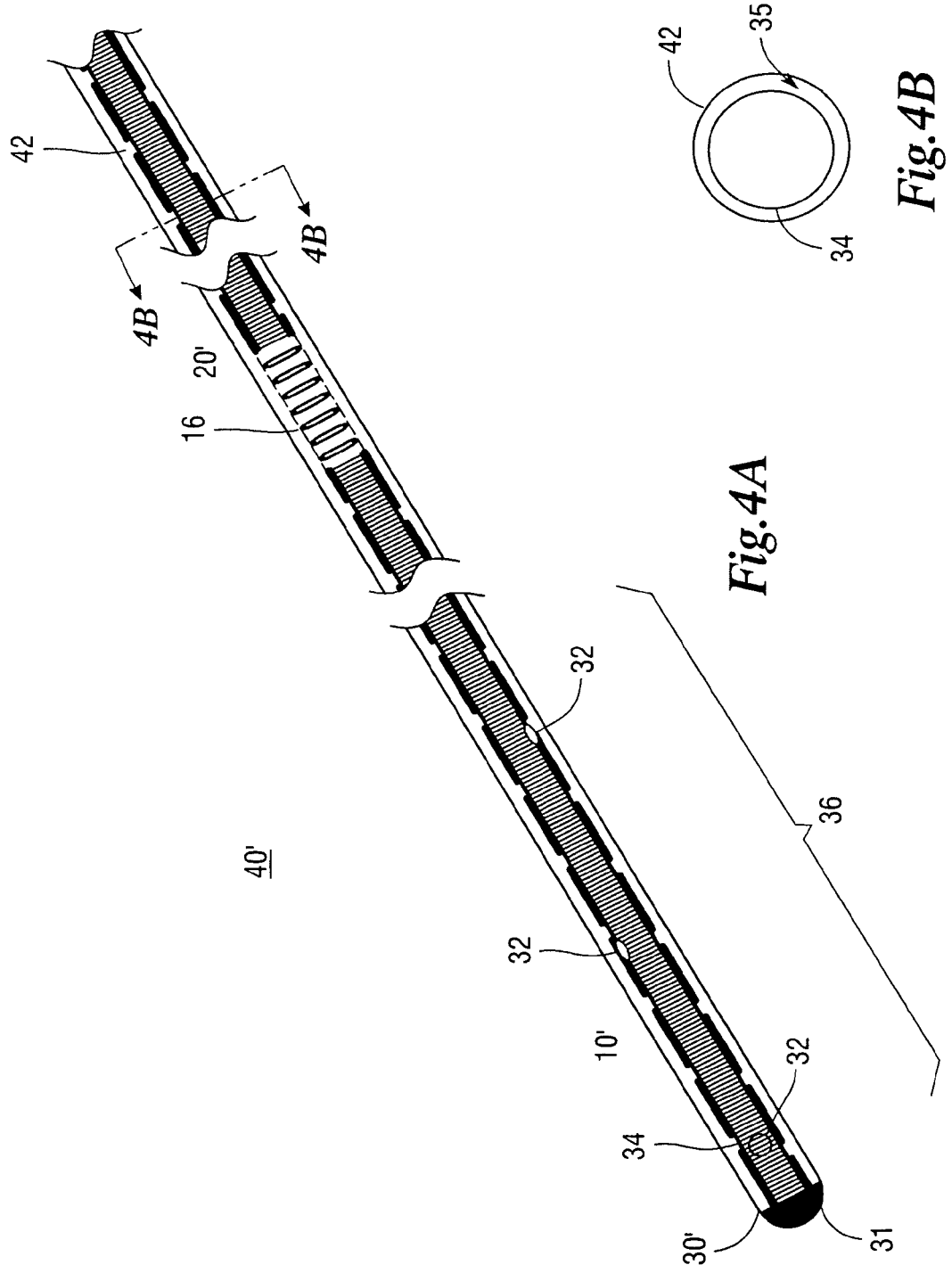

ANESTHESIA CONDUCTION CATHETER FOR DELIVERY OF ELECTRICAL STIMULUS

CROSS REFERENCE TO RELATED APPLICATIONS

This application is a continuation-in-part of U.S. application Ser. No. 10/651,728 filed 29 Aug. 2003 now U.S. Pat. No. 7,462,177 entitled "Anesthesia Conduction Catheter", which is a divisional of U.S. application Ser. No. 09/816,440 filed 23 Mar. 2001 entitled "Anesthesia Conduction Catheter," now U.S. Pat. No. 6,676,643, which claims the benefit of U.S. Provisional Application No. 60/191,726 filed 24 Mar. 2000, now expired, the entirety of which is hereby incorporated by reference.

FIELD OF THE INVENTION

This invention relates in general to catheters, and more specifically, to anesthesia conduction catheters, such as epidural catheters and catheters used for local or regional anesthesia and peripheral pain management.

BACKGROUND OF THE INVENTION

Local or regional anesthesia consists of injecting an agent about the nerves thereby producing a loss of sensation in a region or regions of the body. An example of local or regional anesthesia is an epidural block given to women to ease the pain of childbirth.

Peripheral pain management procedures are continuous peripheral nerve blocks which can be categorized into two types depending on the area of the body where the block is introduced. In upper extremity blocks, the majority of the continuous peripheral nerve blocks performed are in the brachial plexus, i.e., the shoulder and neck regions. Such nerve blocks in the area of the brachial plexus include: interscalene block, supraclavicular block and axillary block.

In lower extremity blocks, the majority of the continuous nerve blocks performed are in the lumbar plexus and the celiac plexus, i.e., the hips and waist areas. Nerve blocks performed in the region of the lumbar plexus are: sciatic block, femoral block, lateral femoral block, obturator block, popliteal block, ankle block and lumbar sympathetic block. Nerve blocks performed in the area of the celiac plexus include: the celiac plexus block, which blocks the splanchnic nerve bundle.

Continuous epidural anesthesia is a technique used to relieve acute and chronic pain, in which an anesthesiologist introduces a conduction catheter via an epidural needle into the patient's epidural space between T10 and L4. The catheter is advanced and checked for "flashback" to indicate whether the distal end of the catheter is properly emplaced in the patient, the needle is removed, and anesthesia is administered. The anesthesia blocks nerve impulses from nerves in the T10 (thoracic vertebra number 10) through S5 (sacral vertebra number 5) region.

The most popular epidural catheter currently in use is a closed-end, non-reinforced catheter with three to five side ports. The preference for the closed end catheter with side ports is due to lowered incidences of inadequate analgesia, i.e., improved drug dispersion, and less need for catheter manipulation. However, a significant drawback to using this type of catheter is the lack of reinforcement that makes the catheter prone to collapsing and/or kink formation during use. Kink formation can make proper placement of the catheter difficult.

To avoid the problems of catheter collapse and kinking associated with closed-end catheters, many anesthesiologists prefer to use a reinforced catheter. Reinforcement may come from a variety of sources including the incorporation into the catheter of wire, polymers, metallic ribbons and the like. A major drawback limiting the use of reinforced catheters is that these catheters are open-ended, which may result in the reinforcement, i.e., the wire or metallic ribbon, becoming detached from inside the catheter and presenting a puncture hazard to the patient. Open-ended catheters were also found in at least one study to provide a less even distribution of analgesia than closed-end catheters (See: *Epidural catheters for obstetrics. Terminal hole or lateral eye? Reg. Anesth.* November-December; 19 (6):378-85, 1994).

A number of inventions have been directed to solving this problem. For example, U.S. Pat. No. 3,757,768 issued to Kline provides an example of a catheter with the helices of a reinforcing spring embedded into the inner wall. Although this catheter can resist collapse of the catheter wall, it may be prone to kink formation because the spring is part of the catheter and cannot relieve torsional stress accumulated from inserting and advancing the catheter into a patient.

U.S. Pat. No. 3,942,632 issued to Cook provides a catheter consisting of an inner core wrapped by a spiraling fiber glass reinforcement surrounded by an outer core. The layered nature of this construction may help prevent catheter wall collapse but may not permit the release of torsional stress and therefore may not make the catheter resistant to kink formation.

U.S. Pat. No. 5,004,456 issued to Botterbosch et al. provides a catheter with a relatively soft distal portion joined to a relatively stiff portion to help prevent catheter wall collapse. This catheter does not provide reinforcement at the distal portion where it may be needed and further does not make any provision for kink resistance.

U.S. Pat. No. 5,947,940 issued to Beisel provides a catheter that is reinforced with a coil made of plastic ribbons. The reinforcing coil is incorporated directly into the catheter's body by being layered between an inner and outer core. The reinforcing coil can be wound less tightly to allow fluid to flow out of side holes in the catheter wall to provide a more even distribution of anesthesia. Although this catheter can provide resistance to catheter wall collapse, the invention of Beisel does not provide for kink resistance because of its construction incorporating the reinforcing coil directly into the catheter. Beisel teaches at col. 4, lines 4-6, that, "(i)t is impossible to terminate the coil short of the side holes since the unsupported, thin polyurethane tube would then kink or collapse and occlude."

In addition to the problems of collapsing and kinking, proper location of the tip of the catheter, and hence the dispensing portion of the catheter, can also be a problem. X-rays can be used to locate a catheter's position, assuming that the catheter has at least some radiopaque components. However, transporting a patient to an x-ray machine, or waiting for the delivery of a portable x-ray machine to the patient, can result in the delay of the delivery of needed medication.

SUMMARY OF THE INVENTION

The present invention is directed to a catheter comprised of a flexible cylindrical tube defining a proximal portion and a distal portion terminating in a distal tip. The tube has a plurality of openings formed therethrough to form a diffusion area. The catheter includes a conductive end cap closing the distal tip. A flexible conductive member is attached to the conductive end cap and extends to the proximal portion. The member is movable within the tube.

The present invention is also directed to a catheter comprising a flexible cylindrical tube defining a proximal portion and a distal portion. The tube has a plurality of openings formed therethrough and a closed end. A flexible conductive coil is attached to an inside diameter of the tube at the proximal and the distal portions so as to form an annular area between an outside diameter of the coil and the inside diameter of the tube. The coil has adjacent turns spaced to enable fluid to leak into the annular area.

The present invention is also directed to a catheter comprised of a flexible cylindrical tube defining a proximal portion and a distal portion. The tube has a plurality of openings formed therethrough and a distal tip. A conductive end cap closes the distal tip. A flexible conductive coil is attached to the conductive end cap and to an inside diameter of the tube at the proximal portion so as to form an annular area between an outside diameter of the coil and the inside diameter of the tube. The coil has adjacent turns spaced to enable fluid to leak into the annular area.

The present invention is also directed to a method of making a catheter comprising: attaching a flexible conductive member to a conductive end cap; forming a diffusion area in a flexible cylindrical tube, the tube defining a proximal portion and a distal portion terminating in a distal tip; surrounding the flexible conductive member with the flexible cylindrical tube such that the end cap closes the distal tip; and attaching the flexible conductive member at the proximal end of the flexible cylindrical tube such that the member is movable within the flexible cylindrical tube.

The present invention is also directed to a system comprising: a catheter of any of the previously mentioned constructions; a needle; a flexible delivery sheath carrying the catheter; an electrical connector; and a removable stylet. A portion of the stylet is carried within the catheter, and an end of the stylet that is opposite to the portion carried within the catheter is connected to the electrical connector.

The present invention is also directed to a method of placing a stimulating catheter comprising: inserting a needle into a patient; applying an electrical stimulus to the needle; feeding a stimulating catheter having a stylet extending thereinto, into the needle, the stylet being in electrical communication with the catheter; applying an electrical stimulus to the stylet; and removing the stylet from the catheter.

The present invention is also directed to a restimulating device, comprising a stylet and an electrical connector having one end adapted for connection with a source of electrical stimulus and another end connected to the stylet.

The present invention is also directed to a method of verifying the placement of a stimulating catheter, comprising: inserting a stylet into a catheter through a connector connected to one end of the catheter, the catheter of the type having a conductive member running substantially the length of the catheter; and applying an electrical stimulus to the stylet.

BRIEF DESCRIPTION OF THE FIGURES

The present invention will now be described for the purpose of illustration and not limitation in conjunction with the following figures wherein:

FIG. 1 is a depiction of the catheter according to one embodiment.

FIG. 2 is an enlarged view of the catheter of FIG. 1 showing the distal portion and flashback window.

FIG. 3A is an illustration of the distal portion of the catheter of FIG. 1 according to one embodiment.

FIG. 3B is a cross-sectional view of the catheter of FIG. 3A.

FIG. 4A is an illustration of the distal portion of a catheter according to another embodiment.

FIG. 4B is a cross-sectional view of the catheter of FIG. 4A.

FIG. 9A illustrates a restimulating device while

DETAILED DESCRIPTION OF THE INVENTION

Figure 5A:
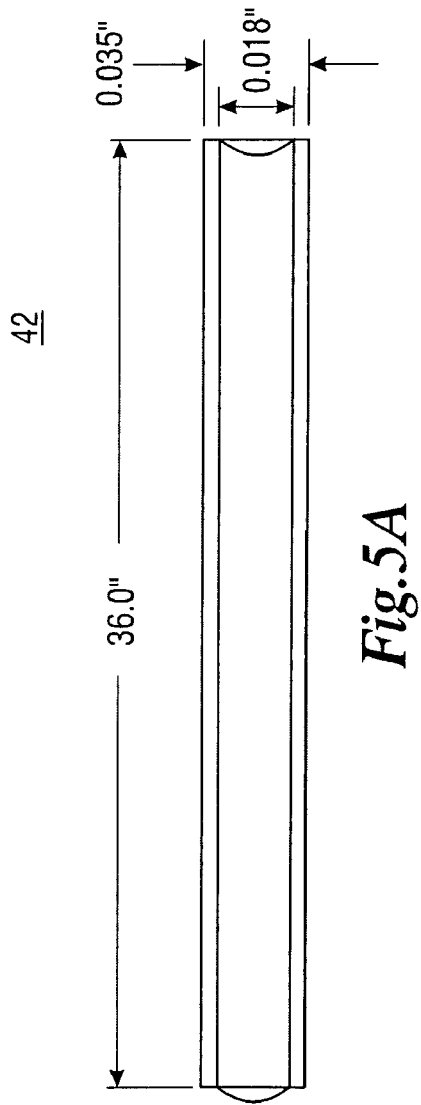
FIGS. 5A and 5B illustrate the component parts and exemplary dimensions for a catheter of the type illustrated in FIG. 4A.

The term "patient" generally refers to living humans and/or animals on which the catheter of the present invention may be employed, but may also include cadavers used for training/teaching purposes.

In the following detailed description, the terms "distal" and "proximal" will be used. As used herein, the term "proximal" refers to that region, portion or end of a device or procedure nearest the person using the device or performing the procedure, while the term "distal" refers to the end opposite of the proximal end.

The catheters of the present invention are intended to be utilized in the introduction of fluids, particularly those fluids containing a pharmaceutically active ingredient, such as anesthesia, into a patient in a wide variety of local, regional and peripheral pain management situations. Such situations, include but are not limited to: interscalene blocks; supraclavicular blocks; auxiliary blocks; sciatic blocks; femoral blocks; lateral femoral blocks; obturator blocks; popliteal blocks; ankle blocks; lumbar sympathetic blocks; and celiac plexus blocks. More than one catheter of the present invention may be used in situations where a temporary block must be administered followed by a longer-term administration of a pharmaceutically active ingredient. Such situations may include, but are not limited to, caesarian section and hernia surgery.

A catheter 40 of the present invention is comprised of a hollow, flexible cylindrical tube 42 defining a closed-end distal portion 10, flashback window 16 and proximal portion 20, is shown in FIG. 1. The flexible cylindrical tube 42 can preferably be about 12 in. (30.5 cm) to about 36 in. (92 cm) in length and preferably has an inner diameter (I.D.) of between about 0.005 in. (0.127 mm) and about 0.020 in. (0.508 mm) with an outer diameter (OD) of between 28 gauge (G) and 16 G, more preferably between 24 G and 18 G, and most preferably 20 G. The thickness of the walls of the flexible cylindrical tube 42 preferably can be from about 0.003 in. (0.076 mm) to about 0.011 in. (0.279 mm). It should be noted that the given dimensions are exemplary and are not intended to limit the scope of the present invention in any way.

Closed-end distal portion 10 is comprised of a distal tip 30 and a diffusion area 36. Diffusion area 36 need not be located in distal portion 10; the diffusion area 36 may be located anywhere along the length of the tube 42 consistent with the intended purpose of the catheter. The diffusion area 36 can be preferably about 0.5 in. (1.27 cm) up to about 20 in. (50.8 cm) in length. The flexible cylindrical tube 42 may preferably have one-centimeter marks 12 plus a mark at distal tip 30, as is commonly practiced in the art. Such marks are typically provided on the catheter 40 to allow the anesthesiologist to easily determine how far the catheter 40 has been inserted into a patient and to confirm the catheter's complete removal from a patient. Proximal portion 20 may include a proximal tip 38.

Optional flashback window 16 can preferably be about 1.0 in. (2.54 cm) in length and is provided to allow the anesthesiologist to visualize blood or cerebrospinal fluid in the catheter 40 upon aspiration, called "flashback" and thereby avoid subarachnoid or intravenous injection of anesthetic.

FIG. 2 depicts an enlarged view of closed-end distal portion 10 and flashback window 16 of the catheter 40 of FIG. 1. A reinforcement member 34 may extend, within the center, along the entire length (or a portion thereof) within the hollow, flexible cylindrical tube 42. For example as illustrated in FIG. 2, the reinforcement member 34 is a coil, sometimes referred to herein as a flexible conductive member 34, that extends from the distal tip 30 to the proximal tip 38 (FIG. 1). The coils of the reinforcement member 34 in distal portion 10 and proximal portion 20 preferably have a spread of up to about 0.015 (0.381 mm) from center to center of the coils. The coils of the reinforcement member 34 in the flashback window 16 region of the catheter 40 of the present invention preferably have a spread of about 0.006 in. (0.152 mm) to about 0.021 in. (0.53 mm) from center to center of the coils.

The flexible cylindrical tube 42 may be made from a variety of sterilizable plastics known to those in the art including, but not limited to, polyamides and copolymers thereof, low density polyethylene, high density polyethylene, polypropylene, polystyrene, polycarbonate, polytetrafluoroethylene, tetrafluoroethylene and fluorinated ethylene propylene. A particularly preferred sterilizable plastic for use in the present invention is nylon polymer. The flexible cylindrical tube 42 may also be made of polyurethanes. Particularly preferred polyurethanes are those incorporating siloxane available as Elast-Eon™ and described in the following patent applications: PCT/AU91/00270; PCT/AU91/00545; PCT/AU98/00497; PCT/AU97/00619; PCT/AU98/00546; and PCT/AU99/00236.

FIG. 3A is an illustration of the closed-end distal portion 10 of the catheter 40 of FIG. 1 according to one embodiment. Distal tip 30 is closed and preferably may be rounded, to prevent reinforcement member 34 from becoming dislodged from the catheter 40 and thereby posing a puncture hazard to the patient. The combination of a closed, rounded tip and the flexibility of the above-mentioned sterilizable plastics helps prevent venous cannulations and/or dura matter punctures.

FIG. 3B is a cross-sectional view of the catheter 40 of FIG. 3A. An annular region 35 is readily visible between the inner diameter of the flexible cylindrical tube 42 and the outer diameter of the reinforcement member 34. However, because the member 34 is free to move within tube 42, the annular region 35 may not be uniform as show in FIG. 3B.

The catheter 40 may be manufactured by combining the flexible cylindrical tube 42 and the reinforcement member 34 such that the reinforcement member 34 is surrounded by the flexible cylindrical tube 42. For example, an end of the reinforcement member 34 may be inserted into the proximal portion 20 of the tube 42, pushed towards the distal portion 10, and attached to the distal tip 30.

The reinforcement member 34 may then be attached to the inside diameter of the proximal portion 20 of the flexible cylindrical tube 42 in a manner such that the reinforcement member 34 remains movable within the reinforcement flexible cylindrical tube 42. An annular area 35 (as best shown in FIG. 3B) is defined by the space between the outer diameter of the reinforcement member 34 and the inner diameter of the flexible cylindrical tube 42. In one embodiment, the reinforcement member 34 may be comprised of a "leaking" coil. The "leaking" coil may have a gap between adjacent turns of the coil. For example, the gap may be between 0.002 in. (0.102 mm) and 0.019 in. (0.483 mm) to allow fluid to continuously leak out from a central portion of the reinforcement member 34 into the annular area 35 between the outer diameter of the reinforcement member 34 and the inner diameter of the flexible cylindrical tube 42. The fluid is then able to exit the catheter 40 via the openings 32 in the diffusion region 16.

Other methods of constructing the catheter 40 may be employed while remaining within the scope of the present invention. The flexible tube 42 may have an axial seam along its length which permits insertion of the reinforcement member 34. The seam may be sealed after the reinforcement member 34 is inserted into the tube 42.

FIG. 4A is an illustration of the distal portion 10' of a catheter 40' according to another embodiment. Open tip 30' is closed by a conductive end cap 31 that is dome-shaped, bullet-nose-shaped, cone-shaped, or any other shape conductive to insertion into a patient. The reinforcement member 34 may be welded or otherwise attached to the conductive end cap 31. Conductive end cap 31 is attached to the hollow, flexible cylindrical tube 42 (which forms the body of the catheter 40' and defines open distal tip 30') to prevent the conductive end cap 31 and/or the reinforcement member 34 from becoming dislodged from the catheter 40' and thereby posing a puncture hazard to the patient. The other end of the reinforcement member 34 may be attached at the proximal end of the tube 42 such that the reinforcement member is free to move within the tube 42.

FIG. 4B is a cross-sectional view of the distal portion of the catheter of FIG. 4A. An annular region 35 is readily visible between the inner diameter of the flexible cylindrical tube 42 and the outer diameter of the reinforcement member 34. However, because the member 34 is free to move within tube 42, the annular region 35 may not be uniform as show in FIG. 4B.

Reinforcement member 34 provides collapse resistance for the catheter during use. The reinforcement member 34 is preferably not embedded in, or in any way attached to, the catheter's inner wall, except at the distal tip 30, 30' and the proximal tip 38, 38'. The lack of attachment allows the reinforcement member 34 to retain its flexibility by being able to move relatively freely within the catheter's body. The flexibility in turn allows the catheter of the present invention to better resist kinking.

The reinforcement member 34 can be made of a variety of materials, including but not limited to stainless steel, titanium, nickel-titanium and plastic monofilament. A particularly preferred material for use in reinforcement member 34 of the catheter of the present invention is stainless steel, such as #304 wire. Although the reinforcement member of the present invention is depicted herein as a coil, the inventor contemplates that it may take a variety of shapes, including but not limited to strips, ribbons, filaments, braids or mesh.

If radiopacity is desired, the reinforcement member 34 preferably can be made of a radiopaque substance such as steel, titanium or nickel titanium or radiopacity can be conferred by the incorporation of barium, bismuth, etc. in the wall of the catheter 40, 40'. Radiopacity, coupled with fluoroscopy, can facilitate easier placement of the catheter of the present invention as is known by those skilled in the art.

Likewise, if transmission of a signal to the distal tip 30' is desired, the reinforcement member 34 can be made of an electrically conductive material.

The diffusion area 36 may have a plurality of openings 32 located therein. For example as illustrated in FIGS. 2, 3A, and 4A, three openings 32 are arranged about 4 mm from each other with the distal most opening being positioned about 5 mm from the distal tip 30, 30'. Each opening 32 may preferably be offset from adjacent openings 32 by about 120° circumferentially to provide for a more even distribution of fluid from the catheter 40,40'. For example, openings of 0.004 inches may be offset 120° circumferentially but within the same plane. It will readily be apparent to those skilled in the art that a greater number of openings 32 and/or openings 32 in different arrangements, sizes and locations can be provided in the catheter 40, 40' of the present invention.

In another embodiment, the openings 32 may be aligned in a straight line or may be in the form of rows. In yet another embodiment, the openings 32 of the catheter of the present invention may be offset from each other by any amount from 0° to 360°. The inventor contemplates that a catheter of the present invention may in some situations have as many as about 100 or more openings in the diffusion area 36. The openings 32 may also be spaced from as little as about 2 m to as much as about 300 mm apart. Although the catheter of the present invention can be sized to be inserted with 16 G to 24 G needles as required by the intended application, it can preferably be sized to permit its insertion using a 16 G to 21 G epidural needle.

Figure 5B:
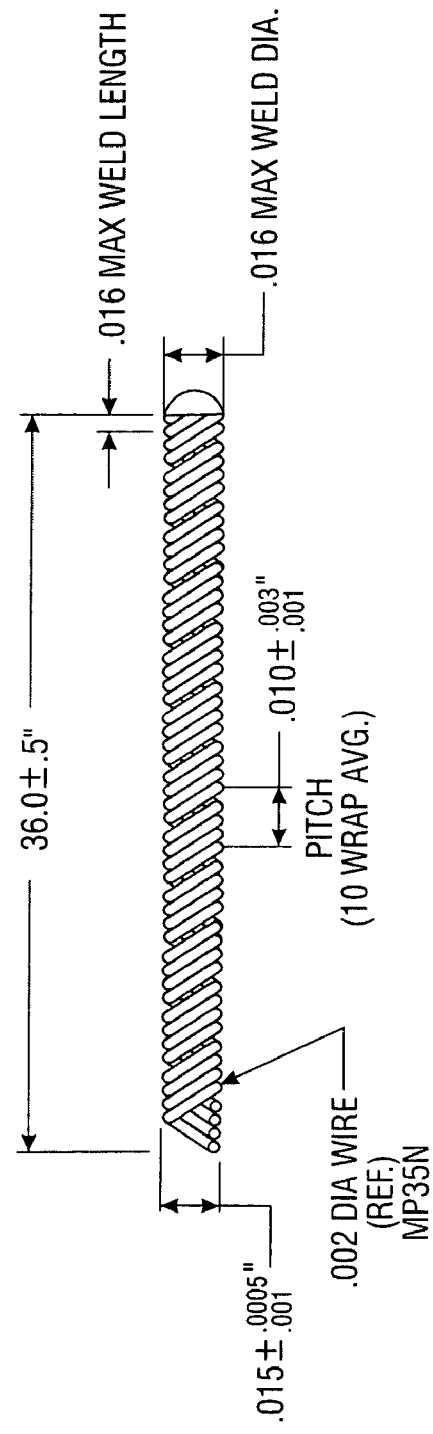

FIGS. 5A and 5B illustrate the component parts and exemplary dimensions for a catheter of the type illustrated in FIG. 4A according to one embodiment. More specifically, a cylindrical tube 42 having a length of approximately 36 in. (914.4 mm), an inner diameter of approximately 0.018 in. (0.4572 mm), and an outer diameter of approximately 0.035 in. (0.889 mm) is illustrated in FIG. 5A. In FIG. 5B, the reinforcement member 34 includes a conductive wire having a diameter of approximately 0.002 in. (0.0508 mm) formed into a quad, right-hand wound coil having a pitch of approximately 0.010 in. (0.254 mm) and an a outer diameter of approximately 0.015 in. (0.381 mm). The conductive end cap 31 is attached to the distal end of the reinforcement member 34. In the current embodiment, the maximum weld length and maximum weld diameter of the conductive end cap 31 is approximately 0.016 in. (0.4064 mm). The overall length of the reinforcement member 34 and the conductive end cap 31 is approximately 36 in. (914.4 mm).

Figure 6A:
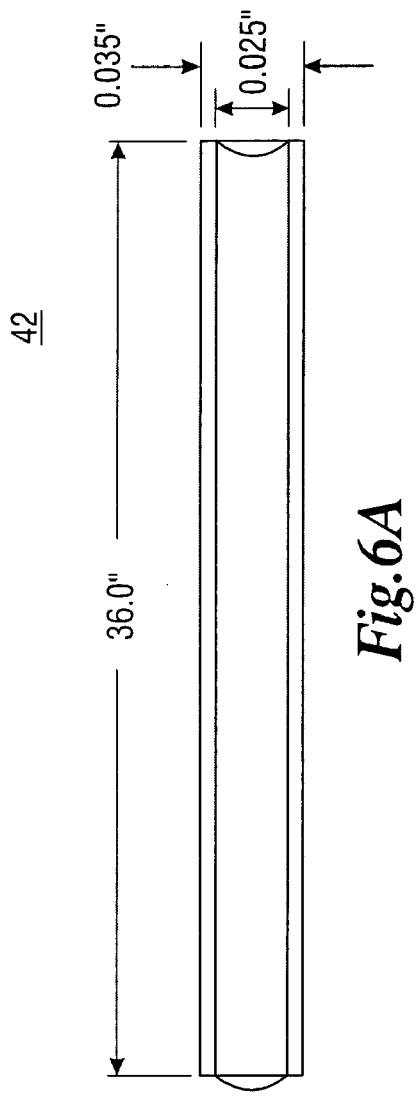
FIGS. 6A and 6B illustrate the component parts and exemplary dimensions for a catheter of the type illustrated in FIG. 4A.
Figure 6B:
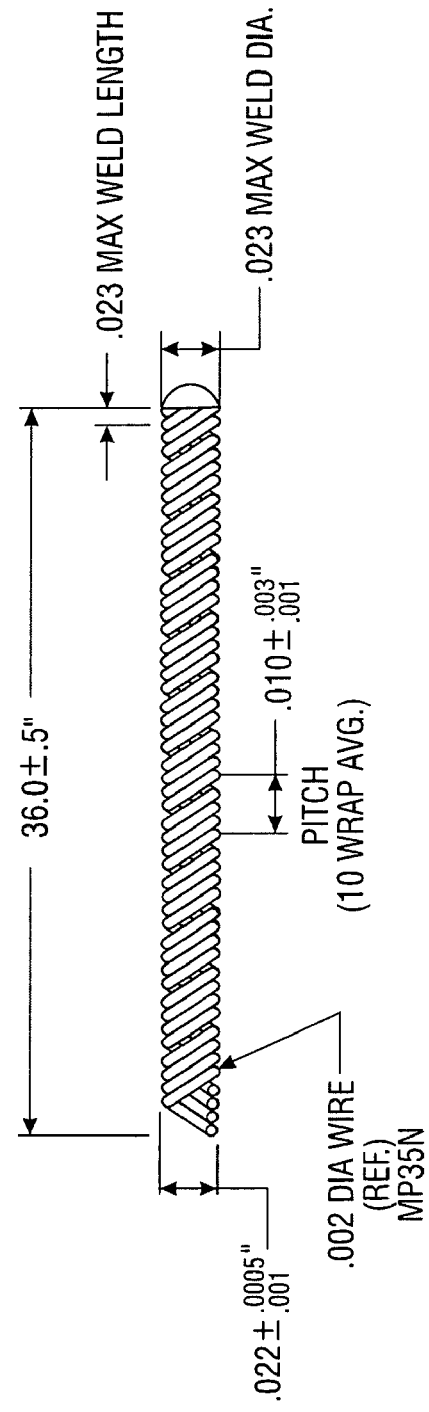

FIGS. 6A and 6B illustrate the component parts and exemplary dimensions for a catheter 40' of the type illustrated in FIG. 4A according to another embodiment. More specifically, a cylindrical tube 42 having a length of approximately 36 in. (914.4 mm), an inner diameter of approximately 0.025 in. (0.635 mm), and an outer diameter of approximately 0.035 in. (0.889 mm) is illustrated in FIG. 6A. In FIG. 6B, the reinforcement member 34 includes a conductive wire having a diameter of approximately 0.002 in. (0.0508 mm) formed into a quad, right-hand wound coil having a pitch of approximately 0.010 in. (0.254 mm) and an a outer diameter of approximately 0.022 in. (0.5588 mm). The conductive end cap 31 is attached to the distal end of the reinforcement member 34. In the current embodiment, the maximum weld length and maximum weld diameter of the conductive end cap 31 is approximately 0.023 in. (0.5842 mm). The overall length of the reinforcement member 34 and the conductive end cap 31 is approximately 36 in. (914.4 mm).

The component parts illustrated in FIGS. 5A-5B and 6A-6B, respectively, may be combined to create a catheter 40' as illustrated in FIG. 4A. The flexible cylindrical tube 42 defines a proximal portion 20' and a distal portion 10'; the distal portion 10' terminating in a distal tip 30'. A diffusion area 36 may be formed in the flexible cylindrical tube 42 within the distal portion 10'. The reinforcement member 34 is attached (for example, welded) to the conductive end cap 31. The reinforcement member 34 is surrounded by the flexible cylindrical tube 42 such that the conductive end cap 31 closes the distal tip 30'. For example, the end of the reinforcement member 34 that is attached to the conductive cap 31 may be inserted into the tube 42 and aligned such that a portion of the conductive end cap 31 extends out of the distal tip 30'. The conductive end cap 31 can then be attached to the tube 42 at the distal tip 30' such that the end cap 31 closes the distal tip 30'.

The flexible conductive member 34 may also be attached to the inside diameter of the proximal portion 20' of the flexible cylindrical tube 42 in a manner such that the flexible conductive member 34 remains movable within the flexible cylindrical tube 42 and is adapted to be connected to a signal source as will be described below. An annular area 35 is defined by the space between the outer diameter of the flexible conductive member 34 and the inner diameter of the flexible cylindrical tube 42. For example in FIGS. 5A and 5B, the annular area 35 is defined as the space between the flexible conductive member 34 having an outer diameter of 0.015 in. (0.381 mm) and the flexible cylindrical tube 42 having an inner diameter of 0.018 in. (0.4572 mm). In FIGS. 6A and 6B, the annular area 35 is defined as the space between the flexible conductive member 34 having an outer diameter of 0.022 in. (0.5588 mm) and the flexible cylindrical tube 42 having an inner diameter of 0.025 in. (0.635 mm). The conductive member 34 may be constructed to enable fluid to leak into said annular area 35. For example, the conductive member 34 may be comprised of a coil having adjacent turns spaced to enable fluid to leak.

Other methods of constructing the catheter 40' may be employed while remaining within the scope of the present invention. For example, the end of the flexible conductive member 34 that is not attached to the conductive end cap 31 may be inserted into the flexible tube 42 relative to the distal portion 10'. The flexible conductive member 34 may be positioned such that a portion of the end cap 31 is inserted into said flexible tube 42 and a portion of the end cap 31 remains exposed. The end cap 31 can then be attached to the flexible tube 42 to close the distal tip 30'. Alternatively, the flexible tube 42 may have an axial seam along its length which may be sealed after the reinforcement member 34 and conductive end cap 31 are inserted into the tube 42. Again, the tube 42 can be sealed at the distal tip 30' such that the conductive end cap 31 closes the distal tip 30'. The method employed to attach the tube 42 to the end cap 31 and/or to the flexible conductive member 34 may be altered while remaining within the scope of the present invention.

Tests were used to determine the percentage of diffusion area through which flow was achieved and the flow rates of catheters of the present invention, and the results are summarized in Table I. The catheters of the present invention tested varied in the length of diffusion area, i.e., the length of catheter measured from the distal end, through which openings may be drilled and therefore through which fluid flow may occur.

Because there is no standard test for catheter flow rates, the inventor used one test, ISO 10555-3:1996 (E), to measure natural, i.e., gravity, flow rates for catheters of the present invention and a pump test to demonstrate achievable flow for the catheter of the present invention using a pump.

Briefly, in the pump test, a Touhy-Borst adapter was attached to the catheter at the proximal end. The catheter was primed with a 3 mL syringe containing distilled water. The outlet line from an appropriate pump (Sorenson or Baxter®), that also contained distilled water was attached to the adapter and the pump was operated. The flow through the diffusion length and the percent diffusion was recorded over a period of 5 to 60 minutes and is reported in Table I.

TABLE I

| Catheter | Length of Diffusion Area in inches (cm) | Percentage of Diffusion Area Through Which Flow Was Achieved | Flow Rate mL/hour | Coil Spread? |
| --- | --- | --- | --- | --- |
| I-A | 1.0 (2.54) | 100 | 0.5 | No |
| I-B | 1.0 (2.54) | 100 | 5.0 | No |
| II-A | 2.0 (5.08) | 78 | 0.5 | No |
| II-B | 2.0 (5.08) | 86 | 5.0 | No |
| III-A | 3.5 (8.89) | 10 | 141.0* | Yes |
| III-B | 3.5 (8.89) | 50 | 38.0* | No |
| IV-A | 5.0 (12.7) | 86 | 5.0 | No |
| IV-B | 5.0 (12.7) | 100 | 125.0 | No |
| V | 7.5 (19.05) | 85 | 5.0 | No |
| VI | 10.2 (25.91) | 70 | 5.0 | No |

*Flow rate measurement made by ISO 10555–3:1996(E).

As can be seen from a review of table I, catheter I provided flow through 100% of its diffusion area at the very slow flow rate of 0.5 mL/hr (I-A) and at 5.0 mL/h (I-B).

Catheter II, with a diffusion area having a length of 2.0 in. (5.08 cm), also showed excellent performance, flowing out of 78% and 86% of the diffusion area, at flow rates of 0.5 mL/hr (II-A) and 5.0 mL/hr (II-B), respectively.

Catheters III-A and B were identical except for the coil being spread in III-A compared to catheter III-B. The data in Table I demonstrate that spreading the coil, as in catheter III-A, resulted in a much higher flow rate, 141 mL/hr, compared to 38 mL/hr for catheter III-B. It should be noted that flow occurred out of only 10% of the diffusion area in catheter III-A compared to 50% in catheter III-B, resulting from the effect of the coil spread in catheter III-A.

Using a diffusion area having a length of 5.0 in. (12.7 cm), resulted in flow occurring out of 86% of the diffusion area at 5.0 mL/hr (IV-A) and out of 100% of the diffusion area at 125 mL/hr (IV-B). This catheter achieved not only a large range of flow rates, but did so with excellent diffusion. As the length of the diffusion area was increased to 7.5 in. (19.05 cm) in catheter V and 10.2 in. (25.91 cm) in catheter VI, flow occurred out of 85 and 70% of the diffusion area, respectively.

The above results demonstrate that catheters of the present invention are capable of flow rates ranging from very low (0.5 mL/hr) to very high (125 mL/hr) with the ability to achieve flow out of 70% to 100% of the diffusion area. The only exceptions to this being catheters III-A and III-B wherein diffusions of 10% and 50% respectively were obtained. However, the inventor contemplates use of catheter III-A in situations where a very high flow rate is required, but where the percentage diffusion is not so important, such as epidural anesthesia.

Although the results summarized in Table I demonstrate that excellent diffusion is obtained in catheters of the present invention having a length of diffusion area as little as 1.0 in. (2.54 cm) to as long an as 10.2 in. (25.91 cm), the inventor contemplates that the length of the diffusion area could be up to about 20 in. (50.8 cm). The results also demonstrate that using catheters of the present invention, control can be achieved over flow rate as well as the diffusion area through which flow occurs.

The conduction catheter of the present invention is intended for administration of local anesthetic or narcotics into intraoperative sites for post-operative pain management and for regional anesthesia outside of the epidural space. Routes of administration may include intraoperative, subcutaneous and percutaneous.

Figure 7:
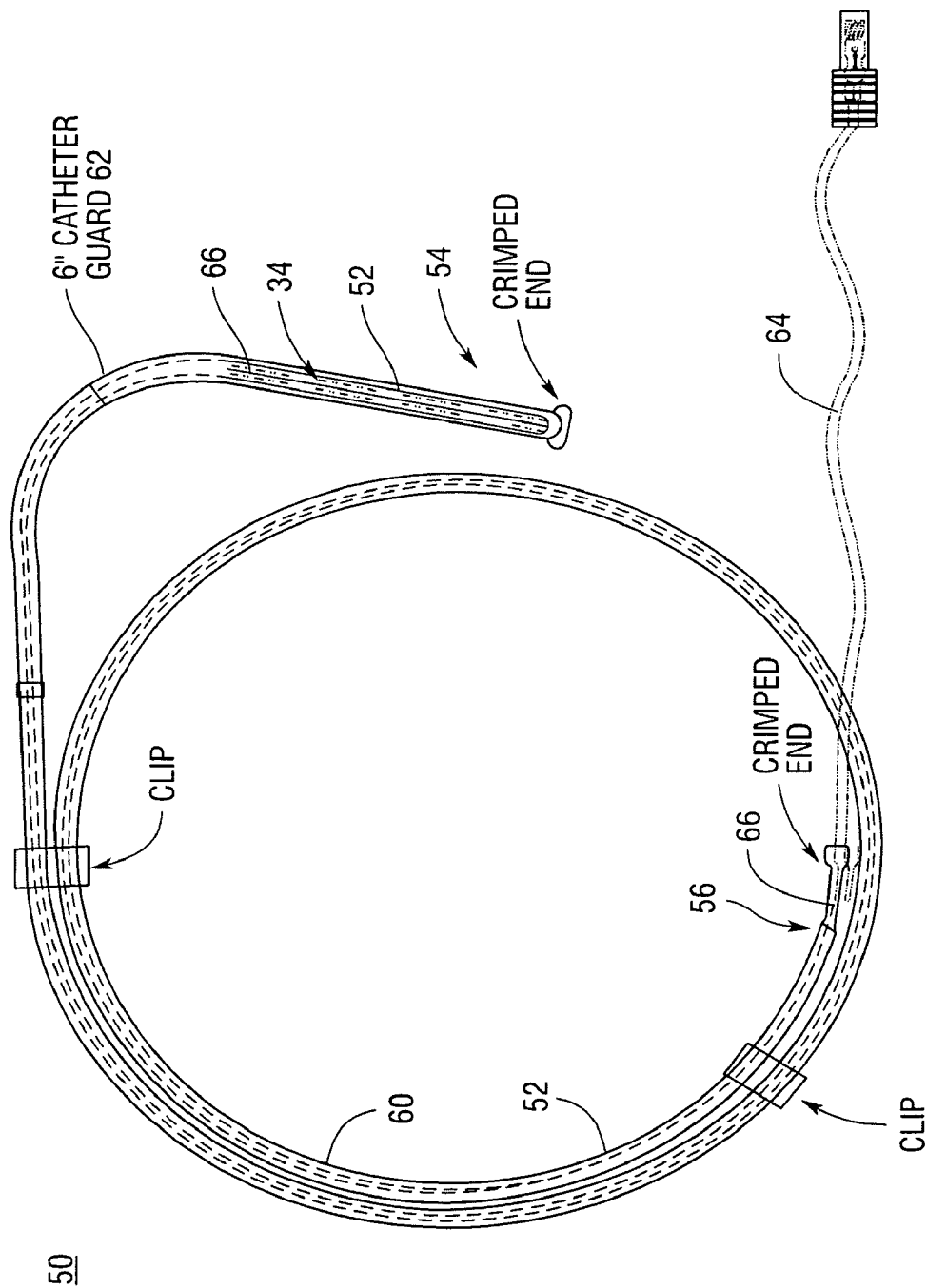
FIG. 7 illustrates a system in which any of the embodiments of the catheter disclosed herein may be used.

FIG. 7 illustrates a system 50 in which any of the embodiments of the catheter disclosed herein may be used. The system 50 includes a catheter 52 (shown in broken lines). The system 50 has a distal end 54 and a proximal end 56. The catheter 52 is carried within a flexible dispenser tube 60 which is one example of a flexible delivery sheath. Approximately six inches of the catheter 52 may extend beyond the dispenser tube 60, with the six inches of the catheter 52 extending beyond dispenser tube 60 covered by a removable catheter guard 62. A removable stylet 66 is inserted into the proximal end of the catheter 52 and extends, in this embodiment, substantially along the entire length of the catheter 52. Extending from the proximal end 56 is an electrical connector 64 which is connected to the stylet 66 as shown in greater detail in FIG. 8A. The removable stylet 66 is substantially carried within the catheter 52 with the end to which the electrical connector 64 is attached being opposite of the end or portion of the stylet 66 carried within the catheter. Also part of the system, but not shown, is a needle.

Figure 10:
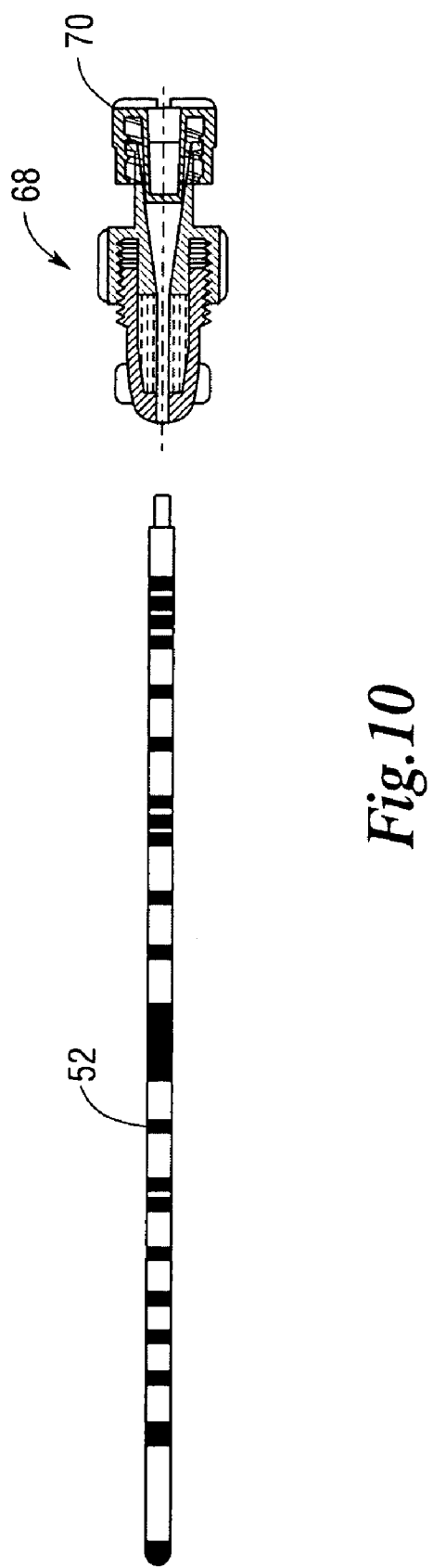
FIG. 10 illustrates a catheter and connector combination.

The present disclosure is also directed to a method of placing the stimulating catheter 52. A needle is inserted into a patient. An electrical stimulus is applied to the needle to insure that the needle is properly inserted. Thereafter, the catheter guard 62 is removed and the exposed end of the catheter is inserted into the needle. The catheter 52 is then pulled out of the dispenser tube 60 as it is being pushed into the needle. During this time, the stylet 66 may remain stationary but, because of its length, the stylet 66 remains in electrical communication with the reinforcing member 34. Thus, the stylet 66 is in electrical communication with the metallic end cap 31. The electrical connector 64 may be attached to a source of stimuli. By applying a stimulus to the electrical connector 64, the stimulus is conveyed to the stylet 66, through the reinforcement member 34 to the metallic end cap 31 to enable the catheter to be precisely positioned. After the catheter is precisely positioned, the stylet 66 is removed, the dispenser tube 60 is removed, and a connector 68 having a removable end cap 70 is connected to the proximal end of the catheter 52 as shown in FIG. 10. In that manner, the end cap 70 may be removed and the connector connected to, for example, a medication device, IV bag, etc. so that fluids may be administered to the patient through the catheter 52.

Figure 8A:
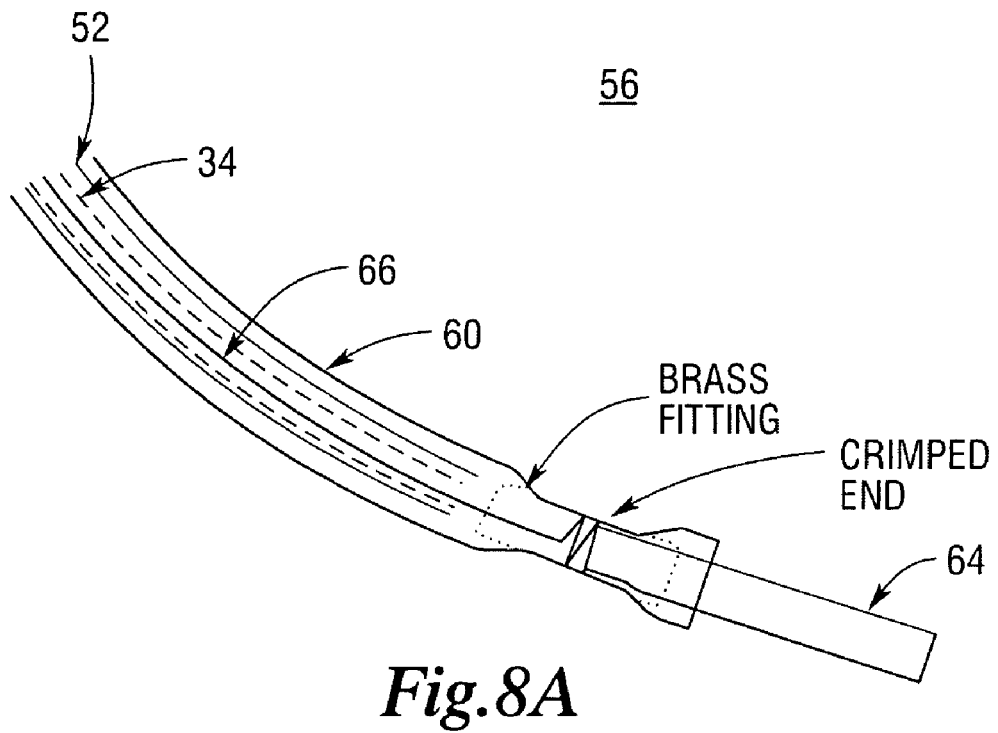
FIGS. 8A and 8B illustrate the details of the proximal and distal ends of the system shown in FIG. 7.
Figure 8B:
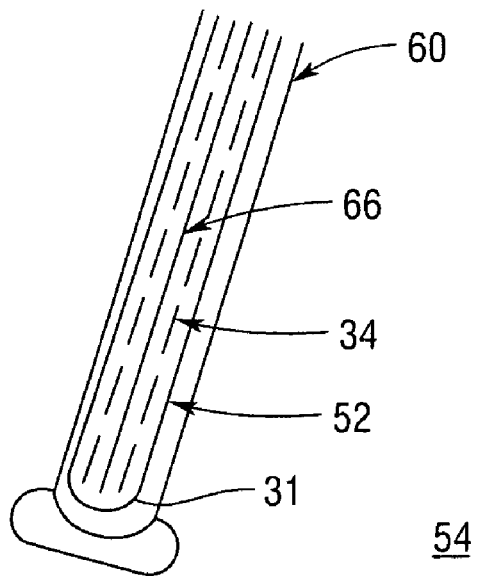

Turning now to FIG. 8, FIG. 8A illustrates the proximal end 56 of the system 50 while FIG. 8B illustrates the distal end 54 of the system 50.

Figure 9A:
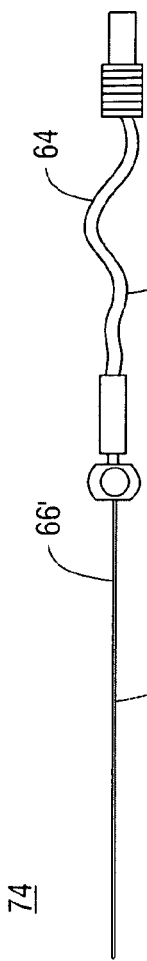
Figure 9B:
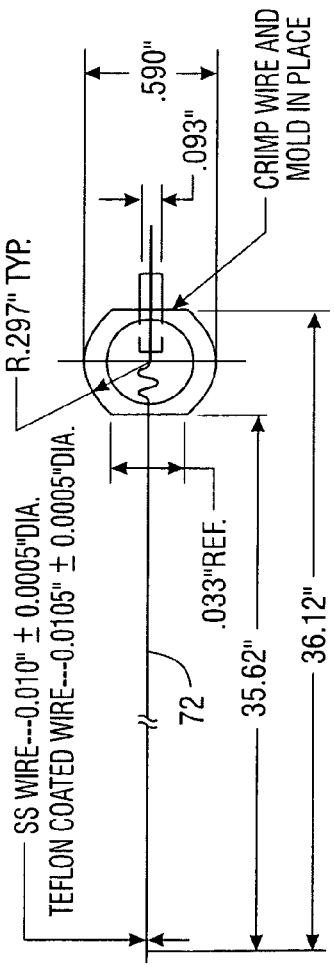
FIGS. 9B and 9C illustrate the restimulating device's component parts.
Figure 9C:
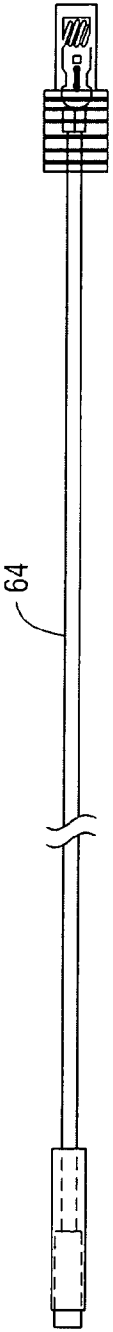

FIG. 9A illustrates a restimulating device 74 comprised of a stylet 66', shown in FIG. 9B as a Teflon coated wire 72, and the electrical connector 64, shown in FIG. 9C. Under certain circumstances, it may be necessary to restimulate the nerves to insure that the catheter 52 has not moved and is still in the proper position. In that case, the stylet 66' of the restimulating device 74 may be inserted into the catheter 52 through the connector 68 by removing end cap 70. Alternatively, if a multi-port connector is used, the stylet 66' of FIG. 9A may be inserted through an unused port. The electrical connector 64 is connected to a source of electrical stimuli and the Teflon coated wire 72 is in contact with the reinforcement member 34 such that electrical stimuli may be conducted to the metallic end cap 31. In that manner, the position of the catheter 52 can be verified and/or adjusted as needed.

The foregoing illustrations of embodiments of the present invention are offered for the purposes of illustration and not limitation. It will be readily apparent to those skilled in the art that the embodiments described herein may be modified or revised in various ways without departing from the spirit and scope of the invention. The scope of the invention is to be measured by the appended claims.

What is claimed is:

1. A stimulating catheter, comprising:
   a flexible cylindrical tube defining an inner diameter, a proximal portion and a distal portion terminating in an open distal tip, said tube having a plurality of openings formed therethrough;
   a dome-shaped conductive end cap closing said open distal tip of said tube; said end cap having a maximum outer diameter not greater than the inner diameter of said tube, and
   a flexible conductive member attached at one end to said conductive end cap and running the length of said tube.

2. The catheter of claim 1 wherein said tube has an inner diameter between 0.005 in. (0.127 mm) and 0.025 in. (0.635 mm).

3. The catheter of claim 1 wherein said tube has an outer diameter between 28 gauge and 16 gauge.

4. The catheter of claim 1 wherein said plurality of openings define a diffusion area.

5. The catheter of claim 4 wherein the length of said diffusion area is between 0.5 in. (1.27 cm) and 20 in. (50.8 cm).

6. The catheter of claim 1 having between 2 and 100 openings.

7. The catheter of claim 1 wherein said openings are offset between 0°-360° circumferentially from adjacent said openings.

8. The catheter of claim 1 wherein said openings are arranged into rows.

9. The catheter of claim 1 wherein said openings are spaced between 2 and 300 mm from adjacent said openings.

10. The catheter of claim 1 further including a window for visualizing flashback.

11. The catheter of claim 1 wherein said flexible cylindrical tube comprises sterilizable plastic.

12. The catheter of claim 11 wherein said sterilizable plastic is selected from the group consisting of polyurethanes, low density polyethylene, high density polyethylene, polypropylene, polystyrene, polycarbonate, polytetrafluoroethylene, tetrafluoroethylene, fluorinated ethylene propylene and polyamides.

13. The catheter of claim 11 wherein said sterilizable plastic comprises polyamide and copolymers thereof.

14. The catheter of claim 11 wherein said sterilizable plastic comprises polyurethane which further includes at least one siloxane.

15. The catheter of claim 1 wherein said flexible conductive member is made from a material selected from the group consisting of stainless steel, titanium, nickel-titanium and conductive plastic filament.

16. The catheter of claim 1 wherein the shape of said flexible conductive member is selected from the group consisting of coil, strip, ribbon, filament, braid or mesh.

17. The catheter of claim 16 wherein said coil is formed of a wire having a diameter of between 0.001 in (0.0254 mm) and 0.003 in (0.0762 mm) and having a pitch between 0.009 in (0.2286 mm) and 0.015 in (0.381 mm) between adjacent coils.

18. The catheter of claim 1, wherein said conductive member is additionally attached to an inside diameter of said tube at said proximal portion so as to form an annular area between an outside diameter of said coil and said inside diameter of said tube, said coil having adjacent turns spaced to enable fluid to leak into said annular area.

19. The catheter of claim 18 wherein said tube has an inner diameter between 0.005 in. (0.127 mm) and 0.025 in. (0.635 mm).

20. The catheter of claim 18 wherein said tube has an outer diameter between 28 gauge and 16 gauge.

21. The catheter of claim 18 wherein said plurality of openings define a diffusion area.

22. The catheter of claim 21 wherein the length of said diffusion area is between 0.5 in. (1.27 cm) and 20 in. (50.8 cm).

23. The catheter of claim 18 having between 2 and 100 openings.

24. The catheter of claim 18 wherein said openings are offset between 0°-360° circumferentially from adjacent said openings.

25. The catheter of claim 18 wherein said openings are arranged into rows.

26. The catheter of claim 18 wherein said openings are spaced between 2 and 300 mm from adjacent said openings.

27. The catheter of claim 18 further including a window for visualizing flashback.

28. The catheter of claim 18 wherein said flexible cylindrical tube comprises sterilizable plastic.

29. The catheter of claim 18 wherein said sterilizable plastic is selected from the group consisting of polyurethanes, low density polyethylene, high density polyethylene, polypropylene, polystyrene, polycarbonate, polytetrafluoroethylene, tetrafluoroethylene, fluorinated ethylene propylene and polyamides.

30. The catheter of claim 18 wherein said sterilizable plastic comprises polyamide and copolymers thereof.

31. The catheter of claim 18 wherein said sterilizable plastic comprises polyurethane which further includes at least one siloxane.

32. The catheter of claim 18 wherein said coil is made from a material selected from the group consisting of stainless steel, titanium, nickel-titanium and conductive plastic filament.

33. The catheter of claim 18 wherein said coil is formed of a wire having a diameter between 0.001 in (0.0254 mm) and 0.003 in (0.0762 mm) and having a pitch between 0.009 in (0.2286 mm) and 0.015 in (0.381 mm) between adjacent coils.

* * * * *